United States Patent
Haro (10) Patent No.: US 6,190,522 B1
(45) Date of Patent: *Feb. 20, 2001

(54) ANALYSIS OF CARBOHYDRATES DERIVATIZED WITH VISIBLE DYE BY HIGH-RESOLUTION POLYACRYLAMIDE GEL ELECTROPHORESIS

(75) Inventor: Luis S. Haro, San Antonio, TX (US)

(73) Assignee: Board of Regents, The University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/066,184

(22) Filed: Apr. 24, 1998

(51) Int. Cl.⁷ .......................... G01N 27/26; G01N 33/00; C07G 17/00; C09B 62/008; C12Q 1/54

(52) U.S. Cl. .......................... 204/461; 204/456; 204/466; 436/94; 436/95; 536/123; 536/55.2; 534/617; 435/14

(58) Field of Search ................................ 435/4, 14, 975; 536/123.1, 55.1, 55.2, 123; 204/461, 456, 466; 436/14, 94, 95; 534/617

(56) References Cited

U.S. PATENT DOCUMENTS

| | | | |
|---|---|---|---|
| 4,874,492 | * 10/1989 | Mackay | 204/461 |
| 5,035,786 | 7/1991 | Brandley et al. | 204/182.1 |
| 5,205,917 | 4/1993 | Klock, Jr. | 204/182.8 |
| 5,258,295 | 11/1993 | Starr et al. | 435/172.3 |
| 5,308,460 | 5/1994 | Mazid et al. | 204/180.1 |
| 5,340,453 | * 8/1994 | Jackson | 204/461 |
| 5,668,272 | * 9/1997 | Prasad | 536/55.3 |

FOREIGN PATENT DOCUMENTS

| | | | |
|---|---|---|---|
| WO 88/10422 | * 12/1988 | (WO) | G01N/27/26 |
| WO 91/05256 | * 4/1991 | (WO) | G01N/33/52 |
| WO 93/02356 | * 2/1993 | (WO) | G01N/33/00 |
| WO 93/05076 | * 3/1993 | (WO) | C08B/37/00 |
| WO 97/02277 | 1/1997 | (WO) . | |

OTHER PUBLICATIONS

Freifelder, ed., *Physical Biochemistry*, pp. 494–499, 537–541, 1982.

Chang, ed., *Physical Chemistry with Applications to Biological Systems*, pp. 147, 173, 174, 1977.

BIO–RAD, "Carbohydrate Electrophoresis Instruments," pp. 155–163. (1993).

Chang, "Binding of Heparin to Human Antithrombin III Activates Selective Chemical Modification at Lysine 236," *Biol. Chem.*, 264:3111–3115, 1989.

Davies and Hounsell, "Carbohydrate chromatography: Towards yoctomole sensitivity," *Biomed. Chromatography*, 10(6):285–289, 1996.

Ding and Vandré, High molecular weight microtubule–associated proteins contain O–linked N–acetylglucosamine, *J. Biol. Chem.*, 271(21):12555–12561, 1996.

El Rassi and Mechref, "Recent advances in capillary electrophoresis of carbohydrates," *Electrophoresis*, 17:275–301, 1996.

Glyko's FACE® Electrophoresis Products, Technology Description, Glyko, Inc., 81 Digital Drive, Novato, CA 94949, (415) 382–6653 (1995).

Guttman and Starr, "Capillary and slab gel electrophoresis profiling of oligosaccharides," *Electrophoresis*, 16(6):993–997, 1995.

Hansson and Karlsson, "Gas chromatography and gas chromatography–mass spectrometry of glycoprotein oligosaccharides," *Methods Mol. Biol.*,14:47–54, 1993.

Haynes et al., "Characterization of oligosaccharides from a glycoprotein variant of human serum albumin (albumin Casebrook) using high–performance anion–exchange chromatography and nuclear magnetic resonance spectroscopy," *Chromatogr.*, 581:187–193, 1992.

Hellerqvist and Sweetman, "Mass spectrometry of carbohydrates," In: *Method Biochem. Anal.*, 34:91–143, 1990.

Honda, "Postcolumn derivatization for chromatographic analysis of carbohydrates," *J. Chromatography*, 720:183–199, 1996.

Hu, "Fluorophore–assisted carbohydrate electrophoresis technology and applications," *J. Chromatogr. A.* , 705(1):89–103, 1995.

Jackson and Williams, "Polyacrylamide gel electrophoresis of reducing saccharides labeled with the fluorophore 8–aminonaphthalene–1,3,6–trisulphonic acid: application to the enzymological structural analysis of oligosaccharides," *Electrophoresis*, 12(1):94–96, 1991.

Jackson, "High–resolution polyacrylamide gel electrophoresis of fluorophore–labeled reducing saccharides," *Methods in Enzymol.*, 230(15):250–265, 1994.

Jackson, "The analysis of fluorophore–labeled glycans by high–resolution polyacrylamide gel electrophoresis," *Analy. Biochem.*, 216:243–252, 1994.

Jackson, "The analysis of fluorophore–labeled carbohydrates by polyacrylamide gel electrophoresis," *Mol. Biotechnol.*, 5:101–123, 1996.

(List continued on next page.)

*Primary Examiner*—Ardin H. Marschel
*Assistant Examiner*—Marjorie A. Moran
(74) *Attorney, Agent, or Firm*—Fulbright & Jaworski L.L.P.

(57) ABSTRACT

The present invention is related to the field of carbohydrate analysis. More particularly, this invention relates to a simple and inexpensive method for analyzing carbohydrates which can be used to separate mono-, di-, tri- and even polysaccharides. More specifically, this invention relates to a quantitative and qualitative method for analyzing carbohydrates that may be present in a biological sample by employing a visible dye or chromophore and high resolution polyacrylamide gel electrophoresis.

40 Claims, 5 Drawing Sheets

OTHER PUBLICATIONS

Karlsson et al., "Strategy for the investigation of O–linked oligosaccharides from mucins based on the separation into neutral, sialic acid– and sulfate–containing species," *Glycoconjugate J.*, 12:69–76, 1995.

Karlsson et al., "High–temperature gas chromatography and gas chromatography–mass spectrometry of glycoprotein and glycosphingolipid oligosaccharides," *Mol. Biotechnol.*, 1:165–180, 1994.

Klockow et al., "The influence of buffer composition on separation efficency and resolution in capillary electrophoresis of 8–aminonaphthalene–1,3,6–trisulfonic acid labeled monosaccharides and complex carbohydrates," *Electrophoresis*, 17:110–119, 1996.

Kovacik et al., "Liquid secondary ion mass spectrometry of methyl glycosides of oligosaccharides using matrices containing carboxamides," *Rapid Commun. Mass Spectrom.*, 10:1661–1667, 1996.

Kyung–Bok et al., "A new method for sequencing linear oligosaccharides on gels using charged, fluorescent conjugates," *Carbohydr. Res.*, 214(1):155–168, 1991.

Larnkjaer et al., "Isolation and characterization of hexasaccharides derived from heparin. Analysis by HPLC and elucidation of structure by $^1$H NMR," *Carbohydr. Res.*, 266:37–52, 1995.

Lee et al., "An electrophoresis–based assay for glycosyltransferase activity," *Anal. Biochem.*, 205(1):108–114, 1992.

Li and Her, "Linkage analysis of chromophore–labeled disacchardies and linear oligosaccharides by negative ion fast atom bombardment ionization and collisional–induced dissociation with B/E scanning," *Analy. Biochem.*, 211:250–257, 1993.

Liu et al., "Ultrasensitive fluorometric detection of carbohydrates as derivatives in mixtures separated by capillary electrophoresis," *Proc. Natl. Acad. Sci. U.S.A*, 88:2302–2306, 1991.

Masada, Skop, Starr, "Fluorophore–assisted carbohydrate electrophoresis (FACE®) for quality control of recombinant–protein glycosylation," *Biotechnol., Appl. Biochem.*, 24:195–205, 1996.

Oefner and Chiesa, "Capillary electrophoresis of carbohydrates," *Glycobiology*, 4(4):397–412, 1994.

Plocek and Chmelik, "Separation of disaccharides as their borate complexes by capillary electrophoresis with indirect detection in visible range," *Electrophoresis*, 18(7):1148–1152, 1997.

Pozsgay and Coxon, "Synthesis and two–dimensional nuclear magnetic resonance analysis of a tetra– and a hexa–saccharide fragment of the O–specific polysaccharide of Shigella dysenteriae type 1," *Carbohydr. Res.*, 257:189–215, 1994.

Reinhold et al., "Carbohydrate sequence analysis by electrospray ionization–mass spectrometry," *Methods Enzymol*, 271(16):377–402, 1996.

Rosenfelder et al., "Chromogenic labeling of monosaccharides using 4'–N,N–dimethylamino–4–aminoacobenzene," *Anal. Biochem.*, 147(1):156–165, 1985.

Stack and Sullivan, "Electrophoretic resolution and fluorescence detection of N–linked glycoprotein oligosaccharides after reductive amination with 8–aminonaphthalene–1,3,6–trisulphonic acid," *Glycobiology*, 2(1):85–92, 1992.

Starr et al., "Fluorophore–assisted carbohydrate electrophoresis in the separation, analysis, and sequencing of carbohydrates," *J. Chromatogr. A.*, 720(1–2):295–321, 1996.

Towbin et al., "Chromogenic labeling of milk oligosaccharides: purification by affinity chromatography and structure determination," *Analy. Biochem.*, 173:1–9, 1988.

Vorndran et al., "Indirect UV detection of carbohydrates in capillary zone electrophoresis," *Chromatographia*, 33(3/4):163–168, 1992.

Weitzhandler et al., "Monosaccharide and oligosaccharide analysis of proteins transferred to polyvinylidene fluoride membranes after sodium dodecyl sulfate–polyacrylamide gel electrophoresis," *Biol. Chem.*, 268:5121–5130, 1993.

Merriam–Webster's Collegiate Dictionary, 10th edition, p. 204. Merriam–Webster, Inc. Springfield, MA. (1996) No month found.*

BIO–RAD catalog, Price List S, pp. 296 and 301. (1993) No month found.*

Neville, D.M. Journal of Biological Chemistry. 246 (20), pp. 6328–6334. (Oct. 1971).*

SIGMA catalog, pp. 37, 91, 376. (1995). No month found.*

Rosenfelder et al. Analytical Biochemistry. 147, pp. 156–165. (1985). No month found.*

* cited by examiner

ANALYSIS OF CARBOHYDRATES DERIVATIZED WITH VISIBLE DYE BY HIGH-RESOLUTION POLYACRYLAMIDE GEL ELECTROPHORESIS

The U.S. government has rights to the use of the present invention pursuant to Grant Nos. GM08194 and GM07717 from the U.S. National Institutes of Health.

1.0 BACKGROUND OF THE INVENTION

1.1 Field of the Invention

The present invention is generally directed to the field of carbohydrate analysis, and more particularly to the analysis of carbohydrates derivatized with a visible chromophoric dye by high resolution polyacrylamide gel electrophoresis. The invention also includes methods and kits for analyzing carbohydrates.

1.2 Description of Related Art

Carbohydrates have many important biological functions. Carbohydrates play important roles in development, immunology and cancer metastasis (Shur, 1994; Wright and Morrison, 1997; Kawaguchi, 1996). Glycoproteins are involved in cell stability and adhesion, antibody recognition, and microorganism binding, and also serve as cell-surface markers (Wyss and Wagner, 1996; Hounsell et al., 1996; Parham, 1996).

Thus, there is substantial interest in carbohydrate analysis. However, a technique for carbohydrate analysis that is both inexpensive and easily performed is currently unavailable. High-sensitivity carbohydrate analysis has been performed with gas chromatography (Karlsson et al., 1995; Karlsson et al., 1994; Hansson and Karisson, 1993), liquid chromatography (Starr et al., 1996; Hu, 1995; Weitzhandler et al., 1993), mass spectrometry (Reinhold et al., 1996; Kovacik et al., 1996; Hellerqvist and Sweetman, 1990), nuclear magnetic resonance spectroscopy (Sugahara et al., 1996; Larnkjaer et al., 1995; Pozsgay and Coxon, 1994; Haynes et al., 1992) and capillary electrophoresis (El Rassi and Mechref, 1996; Oefner and Chiesa, 1994; Liu et al., 1991). However, the above methods of carbohydrate analysis require sophisticated instrumentation and highly trained personnel.

A method for carbohydrate analysis that utilizes polyacrylamide gel electrophoresis to separate fluorescently-labeled carbohydrates has been developed (Jackson, 1996; Jackson, 1994a; Jackson, 1994b) and optimized (Klockow et al., 1996; Masada et al., 1996). However, fluorometers for detection and quantification of the modified carbohydrates are not widely available. Thus, a technique for carbohydrate analysis that is both inexpensive and easily performed is currently unavailable.

2.0 SUMMARY OF THE INVENTION

It is, therefore, a goal of the present invention to provide a simple, inexpensive method for analyzing carbohydrates that does not require the use of a fluorometer. The method of carbohydrate analysis disclosed herein involves the labeling of carbohydrates with a visible dye followed by electrophoretic separation of the dye-labeled carbohydrates. The visible carbohydrate-dye adducts are then identified by their migration or mobilities in the gel and quantified by, for example, densitometric analysis. This method is easy to use and employs commonly available instruments for the separation of the labeled carbohydrates and subsequent analysis.

An embodiment encompasses a method of detecting the presence of a carbohydrate in a sample suspected of containing a carbohydrate by contacting the sample with a chromophore to produce a labeled carbohydrate; separating the labeled carbohydrate from any unreacted chromophore by gel electrophoresis; and detecting the labeled carbohydrate. The identity of any carbohydrates present may then be determined based on its mobility, for example, by a comparison of the migration of the labeled carbohydrate in the gel with known standards, such as known carbohydrates, run under similar conditions. This method allows for the detection and identification of carbohydrates present in the sample in subpicomole quantities.

As used herein "a" will be understood to mean one or more.

The disclosed method typically involves the labeling of carbohydrates, such as mono-, di-, tri-, tetra-, hepta- and even poly-saccharides, with a chromophore. Although the method may be employed to analyze samples containing only one carbohydrate, it may be preferable to employ this method with samples suspected of containing mixtures of two or more carbohydrates.

The chromophore used to label the carbohydrates may be any visible dye capable of derivatizing or labeling the carbohydrate. It should have an absorption maximum in the visible region, which preferably has a high extinction coefficient. Dyes having higher extinction coefficients allow for more sensitive detection. For example, 4-amino-1,1'-azobenzene-3,4'-disulfonic acid ("AABA") has an absorption maximum at 489 nm, with an extinction coefficient of 37,615 which facilitates the visible detection of labeled carbohydrates at low levels (approximately 20 nmol).

The chromophore may also be charged or coupled to a charge-imparting species. It is envisioned that such "charged" chromophores will be particularly useful for the separation and identification of neutral carbohydrates. The charge-imparting chromophore facilitates the labeled carbohydrate's migration in an electric field and thus, the efficient separation by polyacrylamide gel electrophoresis. However, the use of uncharged chromophores is also envisioned particularly for the separation and identification of charged carbohydrates or with the use of additional charged species that may be associated or linked to the uncharged chromophore or carbohydrate.

Embodiments include the labeling of carbohydrates with chromophores such as 4-amino-1,1'-azobenzene or 4'-N,N-dimethylamino-4-aminoazobenzene and their sulfonic acid derivatives. For example, the chromophore may be 4-amino-1,1'-azobenzene-3,4'-disulfonic acid or 4'-N,N-dimethylamino-4-aminoazobenzene-2'-sulfonic acid and the like. Other chromophores which may be employed with aspects of this invention include aminoazobenzene, Direct Red 16, CI Acid Red 57, CI Acid Blue 45, CI Acid Blue 22, CL Mordant Brown 13, and CI Direct Orange 75.

The labeled carbohydrates are produced by contacting the chromophore with the sample under conditions effective to label the carbohydrate with the chromophore by producing a chromophore-dye adduct The carbohydrates may be labeled by any method that is known to those of skill in the art, such as reductive amination and other methods disclosed in U.S. Pat. No. 5,668,272 to Prasad et al., herein incorporated by reference. For example, if a carbohydrate is labeled by a reductive amination process, the reducing end of the sugars are reductively aminated in an aqueous solution with an appropriate chromophore.

The labeled carbohydrates may then be separated by polyacrylamide gel electrophoresis on the basis of size, structure, charge, and hydrophobicity. This method permits the separation of stereoisomers and enantiomers. For example, the sample may contain mixtures of mono-, di-, tri-, and hepta-saccharides; at least two different monosaccharides; mixtures of monosaccharides with their derivatives, such as glucose and glucose derivatives; and combinations thereof.

After the carbohydrates have been labeled, the sample is subjected to polacrylamide gel electrophoresis, or similar electrophoretic separation means, in order to separate and concentrate the carbohydrate-dye adducts into bands. The electrophoresis should be conducted for a time sufficient to allow for separation of the labeled carbohydrate and resolution into bands. This separation step generally results in the separation of the labeled carbohydrates from any unreacted chromophore.

Electrophoresis may proceed past the point where some carbohydrates have been removed from the electrophoresis separation medium. Thus, it may be preferable to proceed with the separation and detection in stepwise fashion. For example, some embodiments include labeling any carbohydrates present with a chromophore; partially separating the labeled carbohydrates from any unreacted chromophore and each other; and then halting the separation and detecting the labeled carbohydrates. The separation of the labeled carbohydrates may then be resumed for subsequent detection steps. Furthermore, these steps may be repeated in stepwise fashion.

The concentration and length of the polyacrylamide gel to be employed depends upon the suspected identity of the carbohydrates to be separated and identified. One of ordinary skill in the art in light of the present disclosure should be able to optimize these parameters based on the actual application involved. For example, samples suspected of containing mixtures of closely related carbohydrates, such as a monosaccharide and its derivatives, may require a longer or more concentrated gel to effect efficient separation. Typically, the gel may have a length of about 8 to about 100 cm, from about 10 to about 50 cm or from about 12 to about 30 cm, with gels having a length of from about 12 to 18 cm, or about 16 cm being preferred. Further, samples suspected of containing different closely related carbohydrates, such as mixtures of monosaccharides, may typically be separated on about a 30 to 40 % gradient polyacrylamide gel while samples suspected of containing carbohydrates of differing lengths may be separated on from about a 25% to a 35%, or a about 30%, polyacrylamide gel. The electrophoresis may also be one- or two-dimensional.

The labeled carbohydrate may be detected by UV-visible spectrometry. The gel may have a length of about 12 cm to about 20 cm.

Although many electrophoretic buffering systems are known in the art and may be employed in the methods and kits described herein, a tris-borate buffering system is generally preferable to effect some carbohydrate separations.

After the labeled carbohydrates have been separated, in whole or part, the carbohydrates may be detected and analyzed by any of the methods used to visualize, detect, or quantify dye-labeled compounds. For example, the gels may be scanned with a densitometer and the visible labeled carbohydrate adducts identified by their mobilities, or migration in the gel being electrophoresed, and quantified by determining their densitometric volume.

Another aspect encompasses kits for analyzing chromogenically-labeled carbohydrates. The kits of the invention provide collections of reagents required for such analysis. An embodiment thus encompasses a kit for analyzing mixtures of carbohydrates having a chromophoric labeling reagent; a precast polyacrylamide gel; an electrophoretic buffer; and a carbohydrate standard. The chromophoric labeling reagent may be any suitable chromophore capable of derivatizing or labeling a carbohydrate for subsequent electrophoretic separation and visualization, for example, 4-amino-1,1'-azobenzene or 4'-N,N-dimethylamino-4-aminoazobenzene and their sulfonic acids. The chromophoric labeling reagent is preferably 4-amino-1,1'-azobenzene-3,4'-disulfonic acid or 4'-N,N-dimethylamino-4-aminoazobenzene -2'-sulfonic acid.

Yet another embodiment encompasses kits and methods employing an oligosaccharide release reagent. In these embodiments, the oligosaccharide release reagent facilitates the releasing of the carbohydrate from any bound components typically prior to reacting the sample with the chromophore. For example, for some applications, it may be desirable to analyze biological samples containing carbohydrates present as glycoconjugates. In these embodiments, it is envisioned that an oligosaccharide release reagent may be employed to chemically or enzymatically release the carbohydrate from a glycoconjugate. The only requirement for the oligosaccharide release reagent is that it should release the carbohydrates in a form capable of being labeled. For example, if the carbohydrates are to be labeled by reductive amination with a chromophore, the release reagent should preserve a free reducing end on the carbohydrate. The choice of release reagent depends on the sample to be analyzed and whether one desires to analyze released oligosaccharides or free monosaccharides that have been hydrolyzed. These release reagents are well known and include deglycosylating enzymes such as EndoH or peptide N-glycosidase; hydrazine; and acids, such as HCl and $H_2SO_4$.

Kits and methods encompassed by the present invention may also include carbohydrate standards. These standards are used for comparative purposes to aid in identifying the sugars present in the sample to be analyzed based on gel mobility under particular conditions. Appropriate standards include any mono-, di-, tri-, tetra-, hepta- and polysaccharides and their derivatives which the sample to be analyzed is suspected of containing or which are similar to any such carbohydrate. The selected standard depends on the suspected identity of the carbohydrates to be analyzed which in turn depends on the particular application. For example, kits encompassed by this invention may be useful for analyzing carbohydrates attached to glycoproteins. In these cases, monosaccharide standards, such as glucose, mannose, galactose, fucose or other monosaccharides, may be employed. Other standards include melibiose, 3-O-methyl-glucopyranose, 2-deoxy-glucose, maltotriose, maltoheptaose, 6-deoxy-glucose, N-acetyl-glucosamine, and N-acetyl-glucosamine 6-sulfate. The standards may be optically pure or may include racemic mixtures of the particular carbohydrate.

3.0 BRIEF DESCRIPTION OF THE DRAWINGS

FIGS. 3A–C show the dependence of saccharide-AABA adduct formation on saccharide concentration.

4.0 DESCRIPTION OF ILLUSTRATIVE EMBODIMENTS

The methods and kits disclosed herein provide an inexpensive and easily performed method of carbohydrate analysis. The described methods and kits are particularly attractive to laboratories that do not have the highly trained personnel nor the expensive equipment needed for other methods of carbohydrate analysis. This method is easy to use and takes advantage of commonly available instruments for the separation of saccharide-dye adducts and subsequent analysis.

The disclosed methods include the labeling of saccharides with the visible dye, 4-amino-1,1'-azobenzene-3,4'-disulfonic acid, which has an absorption maximum of 489 nm, and extinction coefficient of 37,615 to facilitate visible detection at low levels.

The visible dye may be coupled by a reductive amination to different carbohydrates. The labeled carbohydrate adducts are then separated by electrophoresis on alkaline polyacrylamide gels and the gels scanned with a densitometer. The visible sugar-dye adducts is then be qualitatively analyzed by identifying them according to their mobilities and quantified by determining their densitometric volume.

Although any commonly known method may be used to label a carbohydrate with a chromophore, a preferred labeling method encompasses the reductive amination. The kinetics of the reductive amination reaction, performed at 37° C., showed a linear increase in adduct formation from 0 hr to a maximum at 17 hr. A linear dose-response relationship was observed between the amount of carbohydrate (monosaccharide, trisaccharide, heptasaccharide) in the reductive amination reaction and the quantity of sugar-dye adducts that could be detected to a limit of approximately 20 nmol.

Labeled carbohydrates were separated from one another by varying the acrylamide concentration in the polyacrylamide gels. For example, sugar-dye adducts of monosaccharides, disaccharides, trisaccharides and heptasaccharides were separated on alkaline 30% polyacrylamide gels with mobilities of 0.778, 0.667, 0.639 and 0.375. Adducts of glucose, fucose, galactose and mannose were separated with mobilities of 0.844, 0.833, 0.820 and 0.810, respectively, on a 30% to 40% gradient polyacrylamide gel. Adducts of glucose and glucose-derivatives were separated on a 35% polyacrylamide gel.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Materials and Methods

Figure 1A:
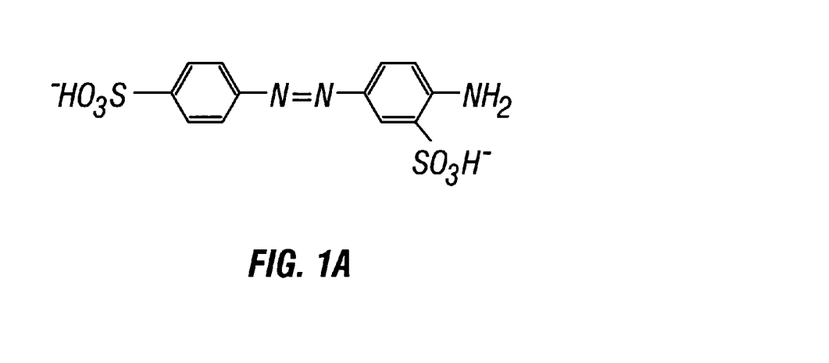
FIG. 1A depicts the structural formula of 4-amino-1,1'-azobenzene-3,4'-disulfonic acid ("AABA").

All carbohydrate sugars were purchased from Sigma Chemical Company (St. Louis, Mo.). The sugars used include were Glc 2, Man, Gal, Mel, 3-O-Glc, dGlc, Fuc, Mt, Mh, 6-dGlc, GlcNAc, and Glc6. Acrylamide and N,N'-methylenebisacrylamide were purchased from Sigma. The visible chromophore, AABA, shown in FIG. 1A, was obtained from Aldrich Chemical Company (Milwaukee, Wis.). A BIO-RAD Protean II Cell with plates allowing for 16 cm long gels was used for polyacrylamide gel electrophoresis. All components of the Tris-borate buffer system were purchased from EM Science.

| Abbreviations | |
|---|---|
| Glc | D-(+)-Glucose |
| Man | D(+)-Mannose |
| Gal | D(+)Galactose |
| Mel | Melibiose |
| 3-O-Glc | 3-O-Methyl-D-Glucopyranose |
| dGlc | 2-Deoxy-D-Glucose |
| Fuc | L(-)Fucose |
| Mt | Maltotriose |
| Mh | Maltoheptaose |
| 6-dGlc | 6-Deoxy-D-Glucose |
| GlcNAc | N-Acetyl-D-Glucosamine |
| Glc6 | N-Acetylglucosamine 6-Sulfate |
| DAAB | 4'-N,N-dimethylamino-4-aminoazobenzene |
| S-DAAB | 4'-N,N-dimethylaminoazobenzene-4-amino-2'-sulfonic acid |
| AABA | 4-amino-1,1'-azobenzene-3,4'-disulfonic acid |

5.2 Example 2

Reductive Amination of Sugars

Figure 1B:
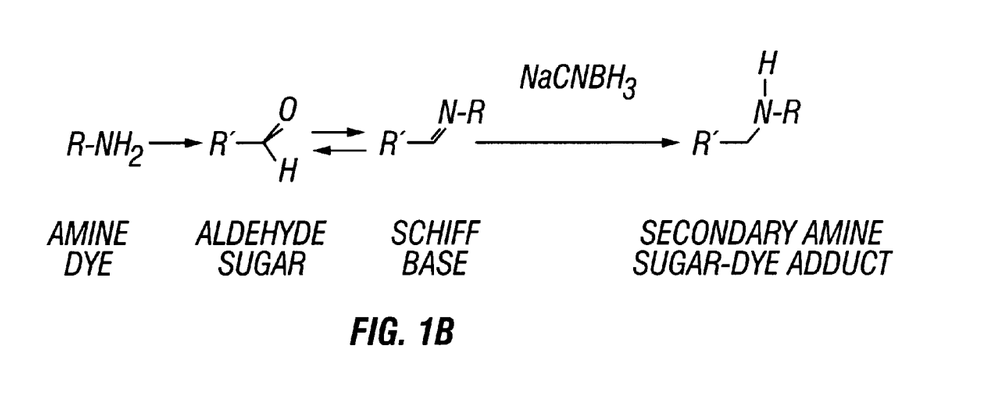
FIG. 1B depicts a reductive amination reaction. Condensation of a sugar possessing an aldehyde reducing carbon and a dye with a primary amino group. The imine (Schiff base) that is reversibly produced is reduced to a secondary amine by $NaCNBH_3$.

The reductive amination of carbohydrates, FIG. 1B, was performed generally as described (Jackson, 1994b), with slight modifications to accommodate aqueous preparations. Dilutions of 1.0 M stock aqueous saccharide solutions were made to provide various concentrations of sugars for the reductive amination reactions. AABA was diluted in acetic acid-water (3:17, v/v) to a concentration of 0.15 M. Five microliters of dye solution were combined with 5 µl of 1.0 M $NaCNBH_3$ (in dimethyl sulfoxide) and 10 µl of a saccharide solution in siliconized microcentrifuge tubes. After incubation at 37° C. for various times, the samples were heated (45° C.) in a dry bath incubator for 15 min to evaporate the solvent. Forty microliters of a glycerol-water (1:4, v/v) solution was added to each sample, which was then stored at 4° C. until analysis by polyacrylamide gel electrophoresis.

5.3 Example 3

Gel Electrophoresis

A Tris-borate buffer system was used to electrophorese the labeled (derivatized) carbohydrates through a polyacrylamide matrix as previously described (Jackson, 1994b), with modifications. The electrophoretic separation system consisted of three components:

1) a resolving gel comprised of 30% (w/v) acrylamide, 1.6% (w/v) N,N'-methylenebisacrylamide, 0.1 M Tris-borate buffer, pH 8.3;
2) a sample gel comprised of 3.9% (w/v) acrylamide, 0.21% (w/v) N,N'-methylenebisacrylamide, 0.1 M Tris-borate buffer, pH 8.3; and
3) an electrode buffer solution comprised of 0.1 M Tris-borate, pH 8.3 which was degassed before use.

After polymerization of the polyacrylamide gels, 4 μl of derivatized sugar samples was loaded into each well and electrophoresed at a constant current of 15 mA per gel and kept at a constant temperature of 4° C. with a refrigerated water bath. After the dye front reached the bottom of the gels (about 6 h), the electrophoresis was terminated.

The gels were preserved by immersion in two drying solutions for 20 min each. The first drying solution was an aqueous solution of 50% ethanol and 5% acetic acid. The second drying solution was an aqueous solution of 30% methanol and 5% glycerol.

5.4 Example 4

Densitometric Analysis

The bands in the gels were analyzed with a BioRad Model GS-700 Imaging Densitometer. The absorption maximum for AABA is 489 nm and it has an extinction coefficient of 37,615. The gels were therefore scanned in the reflectance mode using a blue filter (400 nm–530 nm) at a pixel depth of 12 and at a resolution of 300. The volume determinations for quantification of the amount of sugar-dye adduct formation from each band were performed using BioRad's Molecular Analyst Software.

5.5 Example 5

Separation and Analysis of Chromophor-Labeled Carbohydrates

Figure 2:
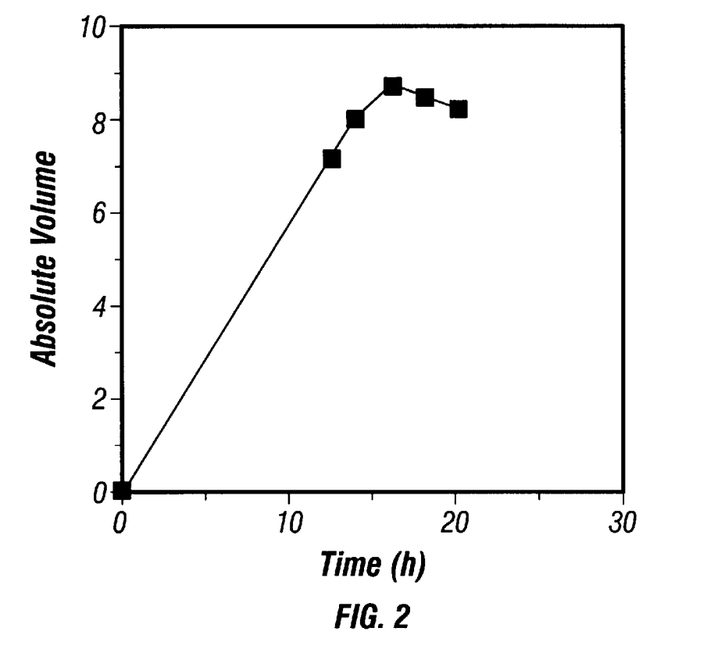
FIG. 2 describes the kinetics of maltotriose-AABA adduct formation.

Kinetics of the formation of sugar-dye adduct were determined. The results are shown in FIG. 2. The absolute volume for sugar-dye adduct formation was plotted as a function of time. The amount of adduct formation increased linearly as a function of time and reached a maximum at 16 hours. All subsequent reactions were therefore carried out for 16 hours.

Figure 3A:
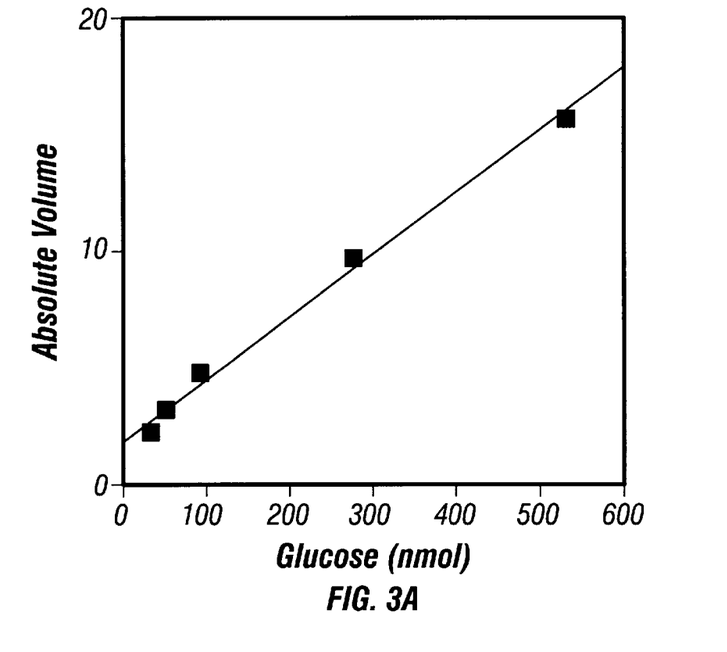
FIG. 3A shows the dependence of glucose-AABA adduct formation on glucose concentration.
Figure 3B:
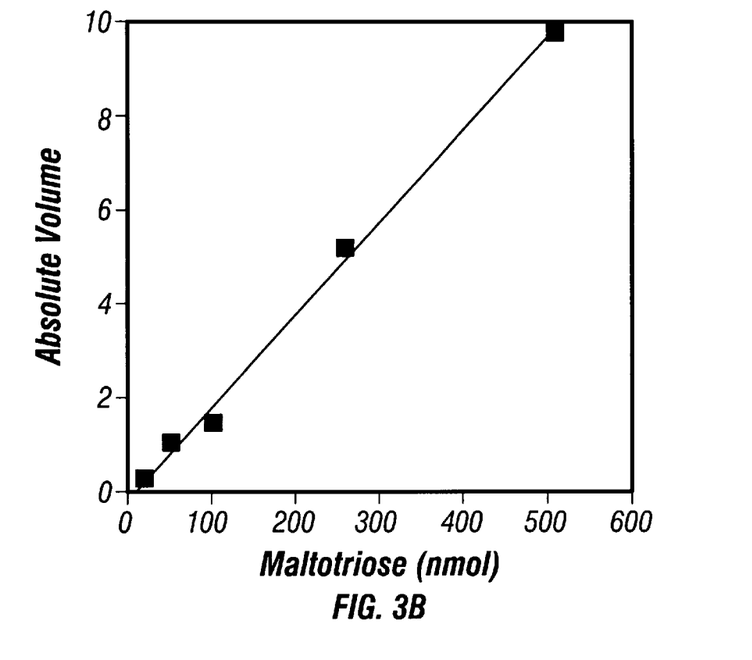
FIG. 3B shows the dependence of maltotriose-AABA adduct formation on maltotriose concentration.
Figure 3C:
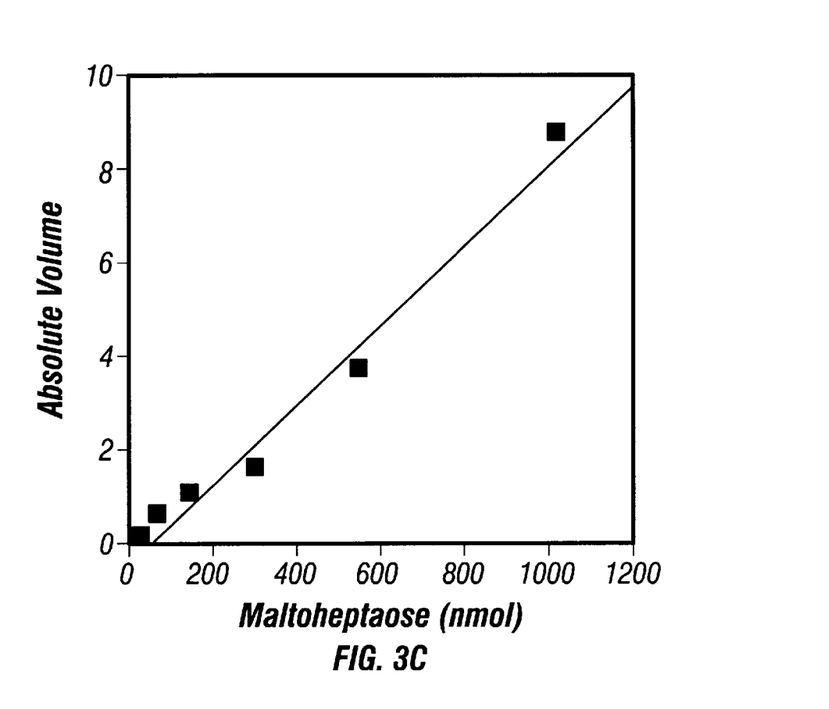
FIG. 3C illustrates the dependence of maltoheptaose-AABA adduct formation on maltoheptaose concentration.

The dependence of carbohydrate-AABA adduct formation on concentration of the carbohydrates in the reductive amination reaction was investigated and the dose-response curves describing this relationship is shown in FIGS. 3A–C. FIG. 3A shows that as the amount of the monosaccharide, glucose, increased from 25 nmol to 500 nmol, the formation of glucose-AABA adduct increased linearly. FIG. 3B shows that as the amount of the trisaccharide, maltotriose, increased from 25 nmol to 500 nmol, the formation of maltotriose-AABA adduct increased linearly. FIG. 3C shows that as the amount of the heptasaccharide, maltoheptaose, increased from 25 nmol to 1000 nmol, the formation of maltoheptaose-AABA adduct increased linearly. The linear regression coefficients correlating the formation of sugar-dye adducts to the amounts of sugar present were 0.996, 0.998 and 0.985 for glucose, maltotriose, and maltoheptaose, respectively.

Figure 4:
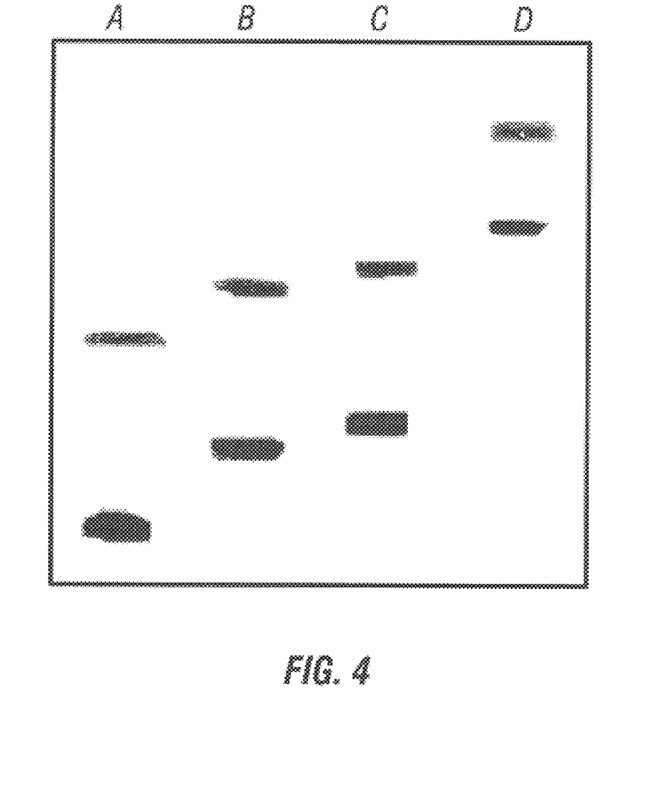
FIG. 4 illustrates the separation of saccharide-AABA adducts of various lengths on a 30% T, 1.6% CBIS polyacrylamide gel at alkaline pH. Lane A, monosaccharide-dye adduct (mannose-AABA); Lane B, disaccharide-dye adduct (melibiose-AABA); Lane C, trisaccharide-dye adduct (maltotriose-AABA); Lane D, heptasaccharide-dye adduct (maltoheptaose-AABA).

Polyacrylamide gel electrophoresis was employed for the analytical separation and identification of AABA-derivatized carbohydrates. Saccharides of various lengths were labeled and the saccharide-AABA adducts separated on a 30% polyacrylamide gel as shown in FIG. 4. Lanes A, B, C and D show the migration of saccharide-AABA adducts for a monosaccharide, a disaccharide, a trisaccharide and a heptasaccharide, respectively. The mobilities of the saccharide-AABA adducts were 0.778, 0.667, 0.639, and 0.375 for the monosaccharide, disaccharide, trisaccharide and heptasaccharide, respectively. Saccharides of various lengths (mono-, di-, tri-, and hepta-) can easily be distinguished from one another because the AABA adducts of the smaller saccharides have greater electrophoretic mobilities than those of the larger saccharides.

Figure 5:
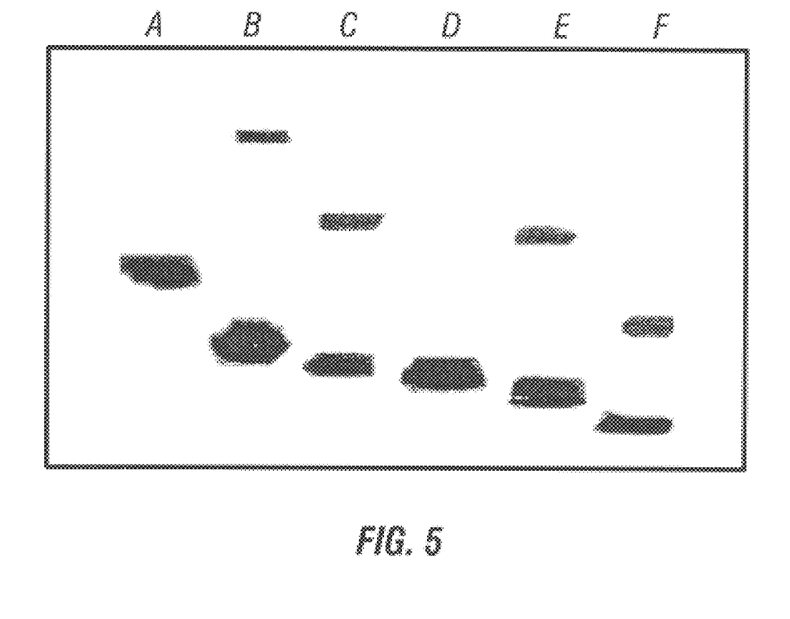
FIG. 5 shows the separation of glucose and glucose derivatives conjugated to AABA on a 35% T, 1.8% $C_{BIS}$ polyacrylamide gel at alkaline pH. Lanes A–F contain AABA adducts of 3-O-methyl-D-glucopyranose, 2-deoxy-D-glucose, N-acetyl-D-glucosamine, D(+)glucose, 6-deoxy-D-glucose, and N-acetylglucosamine 6-sulfate, respectively.

Polyacrylamide gel electrophoresis was used for the separation of AABA adducts of glucose and glucose derivatives. Separation of the saccharide-AABA adducts on a 35% polyacrylamide gel is shown in FIG. 5. Lanes A through F contain AABA adducts of 3-O-Glc, dGlc, GlcNAc, Glc, 6-dGlc, and Glc6 whose mobilities were 0.592, 0.676, 0.690, 0.704, 0.718, and 0.747, respectively. The Rf values for AABA adducts of glucose and its derivatives are distinct and can be used to identify glucose and its derivatives.

Figure 6:
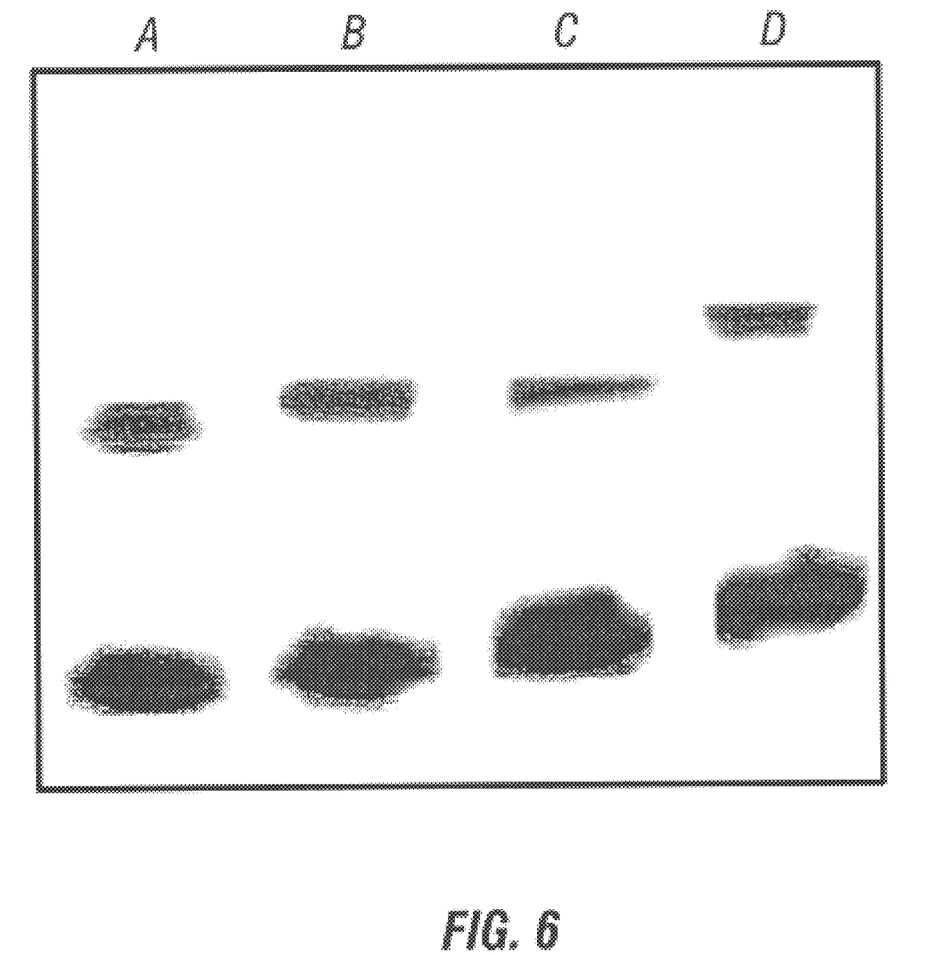
FIG. 6 illustrates the separation of AABA-derivatized monosaccharides on a 30–40% T, 1.6–2.1% CBIS polyacrylamide gel at alkaline pH. Lane A, D(+)glucose; Lane B, L(-)fucose; Lane C, D(+)galactose; Lane D, D(+)mannose.

Polyacrylamide gel electrophoresis was used for the separation of AABA adducts of the common monosaccharides Glc, Fuc, Gal, and Man. AABA conjugated monosaccharides were separated on a 30% to 40% gradient polyacrylamide gel as shown in FIG. 6. Lanes A through D contain AABA adducts of Glc, Fuc, Gal, and Man, whose mobilities were 0.844, 0.833, 0.820 and 0.810, respectively. The Rf values for each monosaccharide-AABA adduct are distinct and can be used to identify the monosaccharides.

Thus, a visible chromophore, AABA, is a useful reagent for both quantitative and qualitative analysis of carbohydrates. The linear dose-responses for the formation of sugar-AABA adducts as a function of sugar concentration show that this method is useful for measuring the amount of sugar in an unknown to approximately 20 nmol. The distinct mobilities of the sugar-AABA adducts in polyacrylamide gels may be used to identify the sugars. The method is useful for analysis of carbohydrates of different sizes as well as for the analysis of monosaccharides.

Derivatized secondary bands can be seen above the primary bands in FIG. 4, FIG. 5, and FIG. 6. These bands appear to be N,O-ketal products generated by addition of sugar hydroxyls to the initially formed Schiff bases. These products would be resistant to reduction by $NaCNBH_3$. Secondary products, identified as tertiary amines by mass spectrometry, were also seen when using the dye DAAB (Rosenfelder et al., 1985). These secondary bands under the conditions employed had no effect on the separation of the sugar-AABA adducts (primary bands).

Several modifications to this basic system are contemplated that may improve the resolution of derivatized sugars and enhance the sensitivity. Increasing the length of the gels can improve separation of derivatized saccharides (Jackson, 1994a). The sensitivity of the detection of sugar-dye adducts is dependent on the extinction coefficient of the dye. The extinction coefficient for AABA is 37,615. Two other dyes, Napththol Blue Black and Direct Blue 71, with extinction coefficients of 48,950 and 45,608, respectively, were tested but did not form adducts. Stearic hindrance may have inhibited the reductive amination reaction with those dyes. The visible chromophore S-DAAB (Chang, 1989) has a structure similar to AABA. This derivative of DAAB may prove to be more useful since it has a slightly higher extinction coefficient (39,000) and less structural hindrance at the reactive amino group by the sulfonate group. Adducts of DAAB are reportedly detectable at 20 pmol (Rosenfelder et al., 1985; Towbin et al., 1988).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6.0 REFERENCES

The following references, to the extent that they provide exemplary procedural or other details supplementary to those set forth herein, are specifically incorporated herein by reference.

Chang, Biol. Chem., 264:3111–3115 (1989).
El Rassi and Mechref, *Electrophoresis*, 17:275–301, 1996.
Hansson and Karlsson, *Methods Mol. Biol.*, 14:47–54 (1993).
Haynes et al., *Chromatogr.*, 581:187–193 (1992).
Hellerqvist and Sweetman, *Method- Biochem. Anal.*, 34:91–143 (1990).
Hounsell et al., *Glycoconjugate J*, 13:19–26 (1996).
Hu, J. *Chromatogr. A.*, 705:89–103 (1995).
Jackson, *Mol. Biotechnol.*, 5:101–123 (1996).
Jackson, *Anal. Biochem.*, 216:243–252 (1994a).
Jackson, *Methods Enzymol.*, 230:250–264 (1994b).
Karlsson et al., *Glycoconjugate J.*, 12:69–76 (1995).
Karlsson et al., *Mol. Biotechnol.*, 1:165–180 (1994).
Kawaguchi, *Rinsho Byori.*, 44:1138–1146 (1996).
Klockow et al., *Electrophoresis*, 17:110–119 (1996).
Kovacik et al., *Rapid Commun. Mass Spectrom.*, 10:1661–1667 (1996).
Larnkjaer et al., *Carbohydr. Res.*, 266:37–52 (1995).
Liu et al., *Proc. Natl. Acad. Sci. U.S.A.*, 88:2302–2306 (1991).
Masada, Skop, Starr, *Biotechnol., Appl. Biochem.*, 24:195–205 (1996).
Oefner and Chiesa, *Glycobiology*, 4:397–412 (1994).
Parham, *Trends Biochem. Sci.*, 21:427–433 (1996).
Pozsgay and Coxon, *Carbohydr. Res.*, 257:189–215 (1994).
Reinhold et al., *Methods Enzymol.*, 271:377402 (1996).
Rosenfelder et al., *Anal. Biochem.*, 147:156–165(1985).
Shur, *Curr. Biol.*, 4:996–999 (1994).
Starretal., *J. Chromatogr. A.*, 720:295–321 (1996).
Sugahara et al., *Eur. J. Biochem.*, 271:12555–12561 (1996).
Towbin et al., *Anal Biochem.*, 173:1–9 (1988).
Weitzhandler, Kadlecek, Avdalovic, Forte, Chow, Townsend, *Biol. Chem.*, 268:5121–5130, 1993.
Wright and Morrison, *Trends Biotechnol.*, 15:26–32 (1997).
Wyss and Wagner, *Curr. Opin. Biotechnol.*, 7:409416 (1996).

What is claimed is:

1. A method of detecting the presence of a carbohydrate in a sample suspected of containing a carbohydrate comprising:
   a) contacting the sample with a non-fluorescent chromophore to produce a labeled carbohydrate, wherein said chromophore comprises 4-amino-1,1'-azobenzene or a sulfonic acid of 4-amino-1,1'-azobenzene;
   b) separating the labeled carbohydrate from any unreacted non-fluorescent chromophore by gel electrophoresis with a gel; and
   c) detecting the labeled carbohydrate.

2. The method of claim 1, further comprising identifying the carbohydrate by measuring migration of the labeled carbohydrate in the gel.

3. The method of claim 2, wherein the carbohydrate is identified by comparing the migration of the labeled carbohydrate with the migration of a standard.

4. The method of claim 3, wherein the standard comprises a known carbohydrate.

5. The method of claim 4, wherein the known carbohydrate is selected from the group consisting of glucose, mannose, galactose, fucose, melibiose, 3-O-methyl-glucopyranose, 2-deoxy-glucose, maltotriose, maltoheptaose, 6-deoxy-glucose, N-acetyl-glucosamine, and N-acetyl-glucosamine 6-sulfate.

6. The method of claim 3, wherein the labeled carbohydrate is quantifiably detected by a densitometer.

7. The method of claim 3, wherein the sample comprises at least two carbohydrates.

8. The method of claim 1, wherein the carbohydrate is detected in subpicomole quantities.

9. The method of claim 1, wherein the chromophore is 4-amino-1,1'-azobenzene.

10. The method of claim 1, wherein the chromophore is a sulfonic acid of 4-amino-1,1'-azobenzene.

11. The method of claim 10, wherein the sulfonic acid of 4-amino-1,1'-azobenzene is 4-amino-1,1'-azobenzene-3,4'-disulfonic acid.

12. The method of claim 1, wherein the sample comprises at least two carbohydrates each separately and independently selected from the group consisting of mono-, di-, tri-, and hepta-saccharides.

13. The method of claim 12, wherein at least two carbohydrates comprise different monosaccharides.

14. The method of claim 13, wherein at least one of the different monosaccharides comprise glucose.

15. The method of claim 1, wherein the carbohydrate is reductively aminated with the chromophore.

16. The method of claim 1, wherein the labeled carbohydrate is detected by visible spectrometry.

17. The method of claim 1, wherein the gel has a length of from about 8 to about 100 cm.

18. The method of claim 17, wherein the gel has a length of from about 12 to about 18 cm.

19. The method of claim 17, wherein the gel is a polyacrylamide gel.

20. The method of claim 19, wherein the gel further comprises a tris-borate buffer.

21. The method of claim 19, further comprising the step of selecting a concentration for the gel depending on a suspected identity of the carbohydrate.

22. The method of claim 21, wherein the sample is suspected of containing different monosaccharides and wherein a sample mixture is separated on about a 30 to 40% gradient polyacrylamide gel.

23. The method of claim 21, wherein the sample is suspected of containing carbohydrates having differing lengths and wherein a sample mixture is separated on from about a 25% to a 35% polyacrylamide gel.

24. The method of claim 1, further comprising releasing the carbohydrate from any bound components with an oligosaccharide release reagent prior to reacting the sample with the chromophore.

25. A method of identifying at least two carbohydrates in a sample comprising:
    a) contacting the sample with a non-fluorescent chromophore to produce labeled carbohydrates, wherein said non-fluorescent chromophore is selected from the group consisting of 4-amino-1,1'-azobenzene or a sulfonic acid of 4-amino-1,1'-azobenzene;
    b) separating the labeled carbohydrates by gel electrophoresis with a gel;
    c) halting the gel electrophoresis;
    d) identifying at least one labeled carbohydrate;
    e) resuming gel electrophoresis; and
    f) identifying at least one labeled carbohydrate;
wherein the carbohydrates are identified by comparing migration of the labeled carbohydrates in the gel with the migration of a standard.

26. The method of claim 25, wherein the standard comprises a carbohydrate.

27. A method of identifying an unknown carbohydrate in a sample comprising:
    a) reductively aminating the carbohydrate with 4-amino-1,1'-azobenzene-3,4'-disulfonic acid to produce a non-fluorescent chromophore labeled carbohydrate;
    b) separating the non-fluorescent chromophore labeled carbohydrate from any unreacted 4-amino-1,1'-azobenzene-3,4'-disulfonic acid by polyacrylamide gel electrophoresis with a polyacrylamide gel;
    c) quantifiably detecting the non-fluorescent chromophore labeled carbohydrate with a densitometer; and
    d) identifying the carbohydrate by comparing the migration of the non-fluorescent chromophore labeled carbohydrate in the gel with the migration of a standard carbohydrate.

28. The method of claim 27, wherein the gel further comprises a tris-borate buffer and has a length of from about 8 to about 20 cm.

29. A kit for detecting carbohydrates comprising:
    a non-fluorescent chromophoric labeling reagent comprising 4-amino-1,1'-azobenzene or a sulfonic acid of 4-amino-1,1'-azobenzene;
    a precast polyacrylamide gel;
    an electrophoretic buffer; and
    a carbohydrate standard.

30. The kit of claim 29, wherein the chromophoric labeling reagent is 4-amino-1,1'-azobenzene.

31. The kit of claim 29, wherein the chromophoric labeling reagent is a sulfonic acid of 4-amino-1,1'-azobenzene.

32. The kit of claim 31, wherein the sulfonic acid of 4-amino-1,1'-azobenzene is 4-amino-1,1'-azobenzene-3,4'-disulfonic acid.

33. The kit of claim 29, further comprising an oligosaccharide release reagent.

34. The kit of claim 33, wherein the oligosaccharide release reagent is selected from the group consisting of a deglycosylating enzyme, hydrazine, and an acid.

35. The kit of claim 34, wherein the oligosaccharide release reagent is a deglycosylating enzyme.

36. The kit of claim 35, wherein the deglycosylating enzyme is EndoH or peptide N-glycosidase.

37. The kit of claim 29, wherein the standard is selected from the group consisting of glucose, mannose, galactose, fucose, melibiose, 3-O-methyl-glucopyranose, 2-deoxy-glucose, maltotriose, maltoheptaose, 6-deoxy-glucose, N-acetyl-glucosamine, and N-acetyl-glucosamine 6-sulfate.

38. The kit of claim 37, wherein the standard is a single enantiomer.

39. The kit of claim 29, wherein the gel has a length of about 12 cm to about 20 cm.

40. The kit of claim 29, wherein the electrophoretic buffer comprises a tris-borate buffer.

* * * * *